US 7,577,988 B2

(12) United States Patent
Fusari et al.

(10) Patent No.: US 7,577,988 B2
(45) Date of Patent: Aug. 18, 2009

(54) METHODS AND APPARATUS FOR FACILITATING EXECUTION OF CONTEXT SHARING APPLICATIONS IN AN ENVIRONMENT WITH A LESS THAN FULLY ENABLED CONTEXT MANAGER

(75) Inventors: David Fusari, Groton, MA (US); Mark Morwood, Bedford, MA (US)

(73) Assignee: Sentillion, Inc., Andover, MA (US)

( * ) Notice: Subject to any disclaimer, the term of this patent is extended or adjusted under 35 U.S.C. 154(b) by 635 days.

(21) Appl. No.: 10/680,009

(22) Filed: Oct. 7, 2003

(65) Prior Publication Data

US 2005/0084105 A1   Apr. 21, 2005

(51) Int. Cl.
G06F 7/04 (2006.01)
(52) U.S. Cl. .................. 726/8; 705/3; 709/203
(58) Field of Classification Search ............ 726/8; 380/213; 705/1–5; 709/202, 203, 217, 229
See application file for complete search history.

(56) References Cited

U.S. PATENT DOCUMENTS 5,974,389 A * 10/1999 Clark et al. .................. 705/3
6,243,816 B1 * 6/2001 Fang et al. .................. 726/5
6,401,138 B1 * 6/2002 Judge et al. ................ 719/328
6,934,740 B1 * 8/2005 Lawande et al. ............ 709/213
7,143,437 B2 * 11/2006 Royer et al. .................. 726/8
2002/0010679 A1 * 1/2002 Felsher ..................... 705/51
2004/0172558 A1 * 9/2004 Callahan et al. ........... 713/201

FOREIGN PATENT DOCUMENTS

WO   WO 00/59286 A   10/2000
WO   WO 01/11464 A2   2/2001

OTHER PUBLICATIONS

International Search Report.

* cited by examiner

Primary Examiner—Kimyen Vu
Assistant Examiner—Suman Debnath
(74) Attorney, Agent, or Firm—Wolf, Greenfield & Sacks, P.C.

(57) ABSTRACT

Method and apparatus for use in a computer system comprising a plurality of applications that share a context and a context manager (CM) to manage the context, wherein the context comprises at least first and second subjects and wherein the CM is configured to enable the plurality of applications to share the first subject but not the second subject. The method and apparatus facilitate execution of the plurality of applications by providing an interface between the CM and the plurality of applications that enables each of the plurality of applications to set the second subject; and by maintaining values for the second subject separately for the plurality of applications so that the second subject is not shared among the plurality of applications.

41 Claims, 3 Drawing Sheets

FIGURE 1

(PRIOR ART)

METHODS AND APPARATUS FOR FACILITATING EXECUTION OF CONTEXT SHARING APPLICATIONS IN AN ENVIRONMENT WITH A LESS THAN FULLY ENABLED CONTEXT MANAGER

FIELD OF THE INVENTION

The present invention relates to techniques for facilitating execution of context sharing applications in an environment with a less than fully enabled context manager.

BACKGROUND OF THE INVENTION

There exist commercial endeavors in which a plurality of computer applications share a set of entities or subjects which are common to the applications. For example, in the field of medicine, a user may provide input describing a given patient to multiple applications. The input may be clinical information, such as x-ray images or blood work results, financial information, such as insurance coverage or billing history, or other types of information. The user's task historically entailed repeating the entry of data into the multiple applications. The data repeatedly entered can be data describing a patient and/or other subjects, such as a user of the system (i.e., to enable "single sign-on" wherein a user logs in to a single network-based resource and is automatically given access to other authorized network-based resources such as other applications), patient, encounters, clinical provider, observations, insurer, or other subjects.

Data which describes a given subject and is used commonly by a plurality of applications is referred to herein as a "context" defined by that subject. The desirability of managing context in the healthcare industry, so that a user need not repeatedly enter information for a subject into multiple applications, has been recognized. To this end, a standard for context management, known as the Health Level 7 (HL7) context management specification, was published in 1999 by the Clinical Context Object Workgroup (CCOW). The CCOW standard defines a context management architecture (CMA) and processes for managing information describing a subject across a range of clinical and other healthcare-related applications. The CCOW standard is defined in HL7 Context Management "CCOW" Draft Standard: Component Technology Mapping: Active X, Version 1.4, January 2002; HL7 Context Management "CCOW" Draft Standard: Technology—and Subject-independent Component Architecture, Version 1.4, January 2002; HL7 Context Management "CCOW" Draft Standard: Subject Data Definitions, Version 1.4, January 2002; HL7 Context Management "CCOW" Draft Standard" Component Technology Mapping: Web/HTTP, Version 1.4, January 2002; and HL7 Context Management "CCOW" Draft Standard: User Interface: Microsoft Windows and Web, Version 1.4, January 2002, all of which are incorporated herein by reference.

Among other features, the CCOW standard defines interfaces for inter-process communication, including communication between applications and a software-based module which coordinates the modification of data across applications (the "context manager"). One embodiment of a context manager is described in commonly-assigned U.S. patent application Ser. No. 09/545,396, entitled "Context Administrator" and Ser. No. 10/632,690, entitled "Methods And Apparatus For Verifying Context Participants In A Context Management System In A Networked Environment", both of which are incorporated herein by reference.

The interfaces ("technology mappings") defined by CCOW provide for communication between the context manager and various "styles" of applications, including those which follow the Microsoft Common Object Model (COM) and Hypertext Transport Protocol (HTTP) conventions, among others. For example, for a COM-based application, the CCOW standard specifies COM interfaces which allow the COM-based application to exchange data and parameters with the context manager when using a CCOW compliant context management system. The interfaces may be programmed to process COM-based data and parameters provided by the context manager and context participant applications to support the context management functions.

Figure 1:
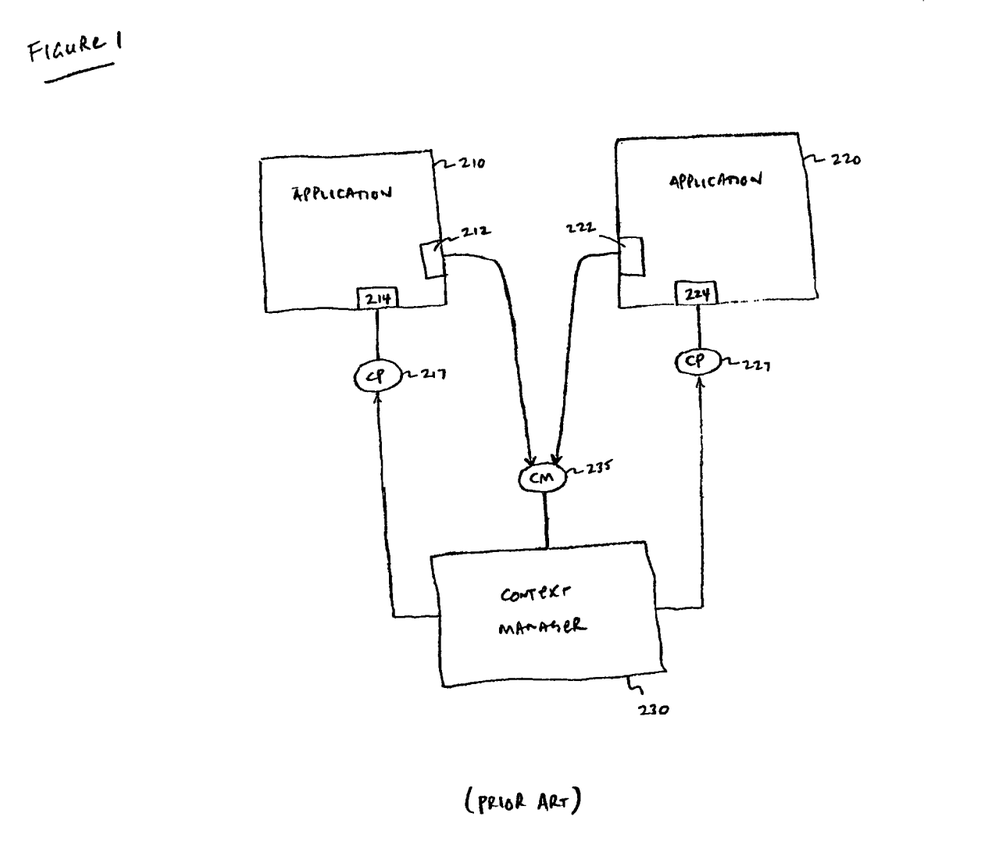
FIG. 1 depicts a prior art implementation of a context manager and a plurality of context participant applications.

FIG. 1 depicts an exemplary context management system, in which a context manager 230 manages context for two context participant applications 210 and 220. Applications 210 and 220 may execute on the same or separate computers, and the computer(s) may be the same or separate from a computer on which context manager 230 executes. Communication between the processes may be enabled via any of numerous combinations of protocols and physical communications devices or components. For example, when the applications 210, 220 and/or the context manager 230 execute on the different computers interconnected by a network (e.g., a local area network), the TCP/IP protocol may be employed.

According to the CCOW standard, communication between the applications in a context and the context manager is facilitated through the use of context participant (CP) interfaces for the applications and a set of context manager (CM) interfaces for the context manager. Each of the CP and CM interfaces may comprise any of numerous suitable components for enabling inter-process communication. In one embodiment, each of the CP and CM interfaces is integrated in an associated application and provides a "plug" which enables communication with the application (e.g., CP interfaces 217, 227 may be implemented within applications 210, 220 respectively, and CM interface 235 may be implemented in an application program executing on the computer on which the context manager 230 executes). In the illustrative system of FIG. 1, the applications 210, 220 have CP interfaces 217, 227, respectively, associated with them.

Context participant (CP) interfaces 217 and 227, respectively, receive communications from context manager 230 on behalf of applications 210, 220. Applications 210, 220 may receive communications from the context manager 230 in a format and style commensurate with the CCOW standard (e.g., as COM messages or HTTP encoded messages over TCP/IP). In the embodiment shown, the communications pass through code portions 214 and 224 associated with the applications. CP interfaces 217, 227 may alternatively be incorporated directly into applications 210, 220 as described above, and directly pass communications thereto. As a further alternative, a CP wrapper or bridge can be provided that performs the function of the CP interface 217, 227, and allows an application to communicate according to the CCOW standard, without requiring any modification of the application itself. Context manager (CM) interface 235 receives communications from applications 210 and 220 and forwards those communications to the context manager 230.

As mentioned above, each of applications 210 and 220 includes a series of programmed routines integrated with the respective application code to perform context management support functions as defined by the CCOW standard. For example, applications 210 and 220 include code portions enabling communication with the context manager. Specifically, within application 210, code portion 212 defines messages sent to the CM interface 235, and code portion 214 implements the CP interface 217. Similarly, application 220 includes code portions 222 and 224 that, respectively, perform the same functions as code portions 212 and 214.

When a user of one of the applications (e.g., application 210) desires to switch the context by changing the data for a subject (e.g., switching from one patient to another), the application sends a request to the context manager 230 (via CM interface 235). The requesting application is referred to as an "instigator" of the requested change in the context.

When the context manager receives a request to change a subject of the context, context manager 230 surveys the other applications in the context (e.g., application 220), to determine whether the switch is acceptable to them. The context manager 230 performs the survey by sending a request to the other applications (e.g., application 220) via their associated CP interfaces. The other applications in the context may determine whether the subject change is acceptable or conditionally acceptable. While rules defining the acceptability of a subject change may be customized for specific applications and contexts, an example of a situation where a requested change may be conditionally acceptable is if data relating to the existing subject has not yet been written to permanent memory on the computer on which the application executes. In this example, the other application may respond to the survey by alerting the instigator that the data could be lost if a change proceeded. The surveyed applications respond to the survey by transmitting messages back to the context manager 230 describing their reactions to the requested change.

According to the CCOW standard, the context manager 230 communicates the results of the survey to the instigator application, and a user thereof examines the results and determines how to proceed. There are a range of options that the user can select, including canceling the requested change, executing the requested change, or removing the instigator application from the context. Any of these options can be selected by the user irrespective of the results of the survey. For example, if one or more of the surveyed applications indicates that the requested change is unacceptable to it, the instigator application may nevertheless force the context change, or alternatively, may simply remove itself from the context so that the instigator application can implement whatever changes it desires without impacting the other applications in the context. After the user decides how to proceed with the requested change, a call is made by the instigator application to the context manager 230 informing the context manager of the change decision. The context manager then makes one or more calls to publish the change decision by notifying the other applications in the context of the decision.

Applications that are compatible with CCOW are conventionally written to support multiple subjects, and assume the existence of a context manager (e.g., 230 FIG. 1) capable of supporting all of the CCOW-defined subjects. Various embodiments of the present invention are directed to techniques for facilitating execution of context sharing applications in an environment with a less than fully enabled context manager.

SUMMARY OF THE INVENTION

One illustrative embodiment of the invention is directed to method for use in a computer system comprising a plurality of applications that share a context and a context manager (CM) to manage the context, wherein the context comprises at least first and second subjects and wherein the CM is configured to enable the plurality of applications to share the first subject but not the second subject. The method facilitates execution of the plurality of applications and comprising acts of: (a) providing an interface between the CM and the plurality of applications that enables each of the plurality of applications to set the second subject; and (b) maintaining values for the second subject separately for the plurality of applications so that the second subject is not shared among the plurality of applications.

Another illustrative embodiment is directed to at least one computer readable medium encoded with instructions for execution in a computer system comprising a plurality of applications that share a context and a context manager (CM) to manage the context, wherein the context comprises at least first and second subjects and wherein the CM is configured to enable the plurality of applications to share the first subject but not the second subject. The instructions, when executed, perform a method of facilitating execution of the plurality of applications, the method comprising acts of: (a) providing an interface between the CM and the plurality of applications that enables each of the plurality of applications to set the second subject; and (b) maintaining values for the second subject separately for the plurality of applications so that the second subject is not shared among the plurality of applications.

A further illustrative embodiment is directed to a context manager (CM) for use in a computer system comprising a plurality of applications that share a context. The context manager comprises at least one processor programmed to manage the context, wherein the context comprises at least first and second subjects. The at least one processor is programmed to: enable the plurality of applications to share the first subject but not the second subject; provide an interface between the CM and the plurality of applications that enables each of the plurality of applications to set the second subject; and maintain values for the second subject separately for the plurality of applications so that the second subject is not shared among the plurality of applications.

DETAILED DESCRIPTION

Aspects of the present invention are directed to techniques for facilitating execution of context sharing applications in an environment with a less than fully enabled context manager. While various embodiments of the present invention are described below in connection with the CCOW standard, the present invention is not limited in this respect, as the techniques described herein can be employed with other types of context sharing systems and standards, including those that share context between applications outside of the healthcare field.

As discussed above, applications (e.g., 210 and 220 in FIG. 1) written to be compliant with CCOW or another specification typically are written for execution in an environment with a fully enabled context manager capable of managing the sharing of all of the supported subjects. However, Applicants have appreciated that in some commercial environments, it may be advantageous to offer customers the option of purchasing one or more versions of a context management system that each enables the sharing of only a subset of the subjects defined by a particular context sharing specification (e.g., a standard), to provide flexibility in the pricing of context management systems to meet the needs of different customers.

For example, Applicants have appreciated that some customers may desire to purchase a context management system that allows the sharing of only the user subject, to enable single sign-on to multiple applications. Alternatively, other customers may wish to purchase a context management system that allows the sharing of all other subjects (e.g., patient, encounters, clinical provider, observation and insurer in a healthcare context) but have no desire to pay more for a single sign-on system that enables the sharing of the user subject. Thus, in accordance with one embodiment of the present invention, a context management system can be provided wherein the context manager 230 does not support the sharing of all subjects defined by a particular context management specification. For example, in one embodiment, the context manager 230 allows the sharing of all CCOW subjects with the exception of the user subject, and in an alternate embodiment the context manager 230 allows the sharing between applications of the user subject but not other subjects defined by CCOW. Again, it should be appreciated that the splitting of subjects into one group including the user subject and another group including all other subjects under the CCOW standard is provided merely for illustrative purposes, as the present invention is not limited in this respect, and can be used to allow numerous other configurations, wherein any subset of subjects can be supported or unsupported in various configurations. In addition, as the references to CCOW are provided merely for illustrative purposes, it should be appreciated that other context management specifications (e.g., standards) can define subjects other than those described herein, and that the present invention is not limited in any respect by the specific subjects that can be supported or unsupported.

Applicants have appreciated that if a computer system employs one or more applications that are configured to share all subjects defined by a context management specification, but the environment employs a context manager that is not enabled to facilitate the sharing of the full set of subjects, problems could be encountered wherein one or more of the applications would not be capable of communicating with the context manager in the way in which the applications expect, which could lead to malfunctioning of the context sharing applications. For example, when a context sharing application is initialized, it may initially seek to communicate with a context manager (e.g., 230 in FIG. 1) to get values for all of the subjects in the context. If the application is unable to get values for all subjects from the context manager, it may assume that it is not being executed in a context sharing system, and may then not seek to share context with other applications, but rather execute in a stand-alone way. An example of this will now be described referring to the user subject in CCOW.

An application executing in the CCOW environment will initially acquire its privileges from the context manager (e.g., 230 in FIG. 1), including privileges relating to the user subject. In this respect, in a CCOW environment wherein the user subject is shared, a single entity (e.g., one of the multiple applications that share the user subject) will be provided with the ability to allow a user to log in to all of the applications, thereby implementing the single sign-on feature. Thus, a CCOW-compliant application may first communicate with the context manager to determine its privileges, including those relating to the user subject. If the context manager is not configured to communicate the user privileges to the application (e.g., if the user subject is unshared), the application may not receive back any indication of its privileges relating to the user subject. This can create problems, as an application that is capable of communicating with a context manager will expect to receive back an indication of all relevant privileges, including privileges for the user subject. Thus, the application may not perceive itself as having the authority to allow a user to log in (e.g., to provide its log in dialog that allows it to authenticate a user), and since the user subject is not shared, it will not be able to get the user subject from the context manager. As a result, the application will not function properly, as no user will be able to log in (either directly or indirectly) to the application.

Another example relates to subjects other than the user subject, an example of which is the patient subject in the CCOW standard. Whether executing in a stand-alone mode or in a context sharing environment, every application typically will be privileged to change other subjects such as the patient subject. One embodiment of the present invention, described in more detail below, is directed to techniques for enabling one or more applications that are enabled to share such a subject to execute properly in an environment that includes a context manager that is not enabled to facilitate the sharing of that subject.

One illustrative embodiment of the present invention will now be described making reference to FIG. 2, which illustrates a context sharing environment wherein two applications 301 and 303 (respectively referred to as Application 1 and Application 2) share a context that includes two subjects, i.e., a patient subject and a user subject. The system further includes a context manager 305 that facilitates the sharing of context between applications 301 and 303. In the illustrative embodiment shown, the context manager 305 is enabled to allow sharing only of the user subject, and does not allow sharing of the patient subject between the applications 301 and 303.

The context manager 305 can allow sharing of the user subject in any suitable manner, as the present invention is not limited in this respect. In the illustrative embodiment shown, the context manager 305 can allow sharing of the user subject in accordance with the CCOW standard to allow single sign-on. In the embodiment shown, application 301 is provided with privileges to set the user subject, as shown conceptually at 307. The context manager stores information at 309 identifying the data value for the user subject, which in FIG. 2 has been set by application 301 as user Y. In addition, the context manager 305 passes along the user subject, set by application 301, to application 303, as shown conceptually at 311. In this manner, applications 301 and 303 share the user subject, and both are shown in the illustrative example of FIG. 2 as having the user subject set to user Y. The application 301 can change the user subject to identify different users in any suitable manner. An example of the communications among applications that share a context and the context manager is provided in the above-referenced applications incorporated herein by reference. However, as mentioned above, the aspects of the present invention described herein are not limited to the CCOW standard or any particular technique for sharing a context subject, and can be employed with any suitable context management standard and/or communication protocol.

Figure 2:
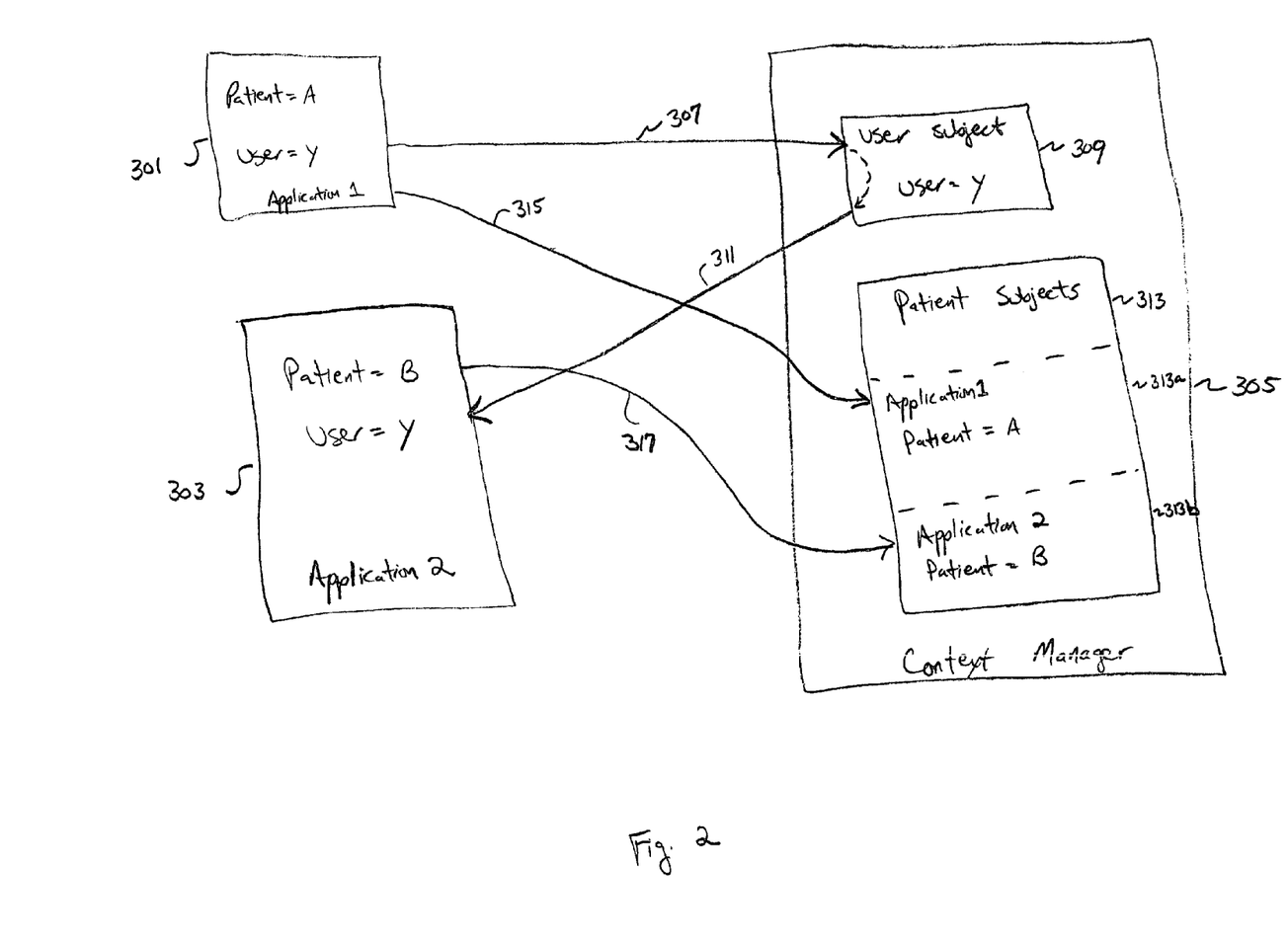
FIG. 2 depicts an illustrative system in which a context manager facilitates execution of two context sharing applications that share a user subject in the context, but in which the context manager does not support sharing of all other subjects of the context, in accordance with one embodiment of the present invention.

In the illustrative example of FIG. 2, the patient subject is not shared. However, as described above, each of applications 301 and 303 is a context sharing application written to operate in an environment wherein all the context subjects (including the patient subject) are shared. Thus, applications 301 and 303 will contact the context manager 305 at different times to seek to change (or set) the patient subject or to get information about the current status of the patient subject. For example, many applications when they are launched will seek information about their current state, and may ask the context manager for the current state of the context subjects. If a particular subject has not yet been set, the application will be so informed.

In accordance with one embodiment of the present invention, an interface is provided by the context manager 305 to allow both of the applications 301 and 303 to set and get the patient subject, but to maintain information relating to the patient subject separately for the applications, so that the patient subject is not shared. This is illustrated conceptually in FIG. 2, wherein the context manager 305 includes information 313 relating to the patient subjects for the applications 301 and 303. As shown in FIG. 2, this patient subject information includes a first set of information 313a that is dedicated to application 301, and a second set of information 313b that is dedicated to application 303. Thus, when application 301 seeks to set the patient subject as shown at 315, only the portion 313a within the context manager 305 is updated, and when application 303 seeks to set (at 317) the patient subject, only the portion 313b is updated. In this manner, separate information relating to the patient subject is maintained for applications 301 and 303, so that each is able to set the patient subject to whatever patient the application desires. However, because the context manager 305 illustrated in FIG. 2 does not support sharing of the patient subject, when one of the applications sets the patient subject, the information is updated within the context manager 305, but that information is not propagated to the other application in the way in which the user subject is propagated at 311 as discussed above. When application 301 contacts the context manager 305 to get the value for the patient subject, the value (identifying Patient A in FIG. 2) is returned from 313a, whereas when application 303 contacts the context manager 305 to get the value for the patient subject, the value (identifying Patient B in FIG. 2) is returned from 313b. Thus, the context manager 305 allows each of the applications 301 and 303 to function properly, by providing an interface for each to set and get the patient subject, but does not allow the patient subject to be shared between these applications.

The precise manner in which the context manager 305 provides interfaces for the applications 301 and 303 to get and set any unshared subjects (e.g., the patient subject in the example of FIG. 2) is dependent upon the nature of the system in which the aspects of the present invention are implemented, and the present invention is not limited in this respect. As discussed above, in connection with the CCOW standard, an application seeking to set or change a user subject provides a request to the context manager to instigate such a change, and then the context manager surveys the other applications in the context and communicates the results to the instigator application. In accordance with one embodiment of the present invention, when one of the applications 301, 303 seeks to change an unshared subject, the context manager 305 need not perform any survey of other applications, as the subject is not shared and is under the exclusive control of the application requesting the change. Therefore, the context manager simply makes the change in the area (e.g., 313a or 313b in FIG. 2) containing information relating to the context subject, and returns information to the instigating application informing it that the requested change is acceptable. Again, the aspects of the present invention described herein are not limited to this or any particular technique for implementing the interface between the applications and the context manager for unshared subjects, as any suitable technique can be employed.

Figure 3:
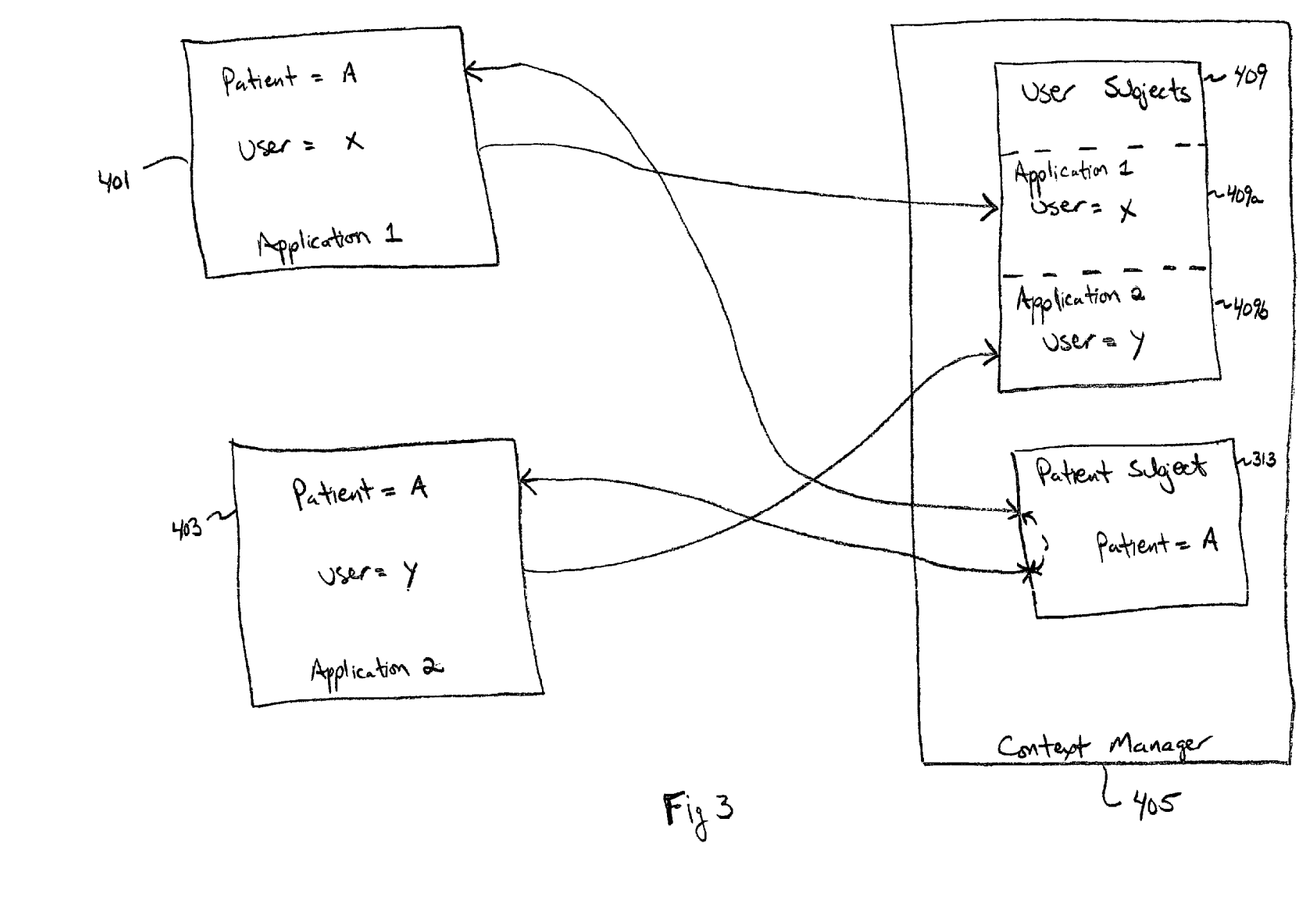
FIG. 3 depicts an illustrative system in which a context manager facilitates execution of two context sharing applications that share at least one subject in a context, but in which the context manager does not support sharing of the user subject of the context, in accordance with another embodiment of the present invention.

FIG. 3 illustrates an alternative illustrative configuration that is similar in some respects to the configuration shown in FIG. 2, but differs in terms of which subject is shared and which is not. In this respect, in the illustrative example of FIG. 3, the context manager 405 enables sharing of the patient subject between two applications 401 and 403, but does not enable sharing of the user subject. Thus, either application 401 or 403 is capable of setting the patient subject, and any changes made thereto are propagated to the other application. Again, this can be accomplished in any suitable manner in accordance with any context sharing standard or protocol, as the aspects of the present invention described herein are not limited in this respect.

In the illustrative example of FIG. 3, the user subject information 409 within the context manager 405 includes a first component 409a dedicated to application 401 and a second component 409b dedicated to application 403. Thus, as shown in FIG. 3, the applications 401 and 403 can have different users (User X and User Y respectively in FIG. 3), as the context manager 405 does not allow sharing of the user subject. This can be accomplished in much the same manner as the non-sharing of the patient subject described above in connection with FIG. 2. However, an additional issue arises in connection with the user subject, as some systems (e.g., CCOW-compliant systems) implement the user subject as a secure subject. In this respect, some systems will provide additional security burdens on an application that seeks to change the user subject for a suite of applications, to prevent a rogue application from spoofing its identity and allowing a change of the user subject to allow an unauthorized user access to sensitive information.

In view of the security concerns raised, applications that are CCOW-compliant do not have the ability to change the user subject unless they first are granted privileges to do so from the context manager 405. Thus, in accordance with one embodiment of the present invention, when the user subject is not shared, the context manager provides each of the applications with the privileges necessary to allow them to set and change the user subject, to ensure that each application will have the ability to allow a user to log in. It should be appreciated that security concerns are lessened when the user subject is not shared.

In the CCOW standard, additional information, referred to as an annotation subject, can be associated with some subjects. Annotation subjects are not set by the applications, but rather, are set by a mapping agent in the system (e.g., within the context manager) based upon information provided from an authoritative source. An example of an annotation subject may be information that identifies a patient's allergies. In accordance with one embodiment of the present invention, annotation subjects are completed by a mapping process in the conventional manner, as the aspects of the present invention related to addressing unshared subjects does not implicate annotation subjects.

As discussed above, the configurations shown in FIGS. 2 and 3 are provided merely for illustrative purposes, as the aspects of the present invention described herein are not limited to such configurations. For example, in each of FIGS. 2 and 3, only two applications participate in the context. It should be appreciated that the aspects of the present invention described herein are not limited in this respect, and can be employed in connection with any number of applications in a context. Similarly, in the illustrative configurations of FIGS. 2 and 3, there is only one shared subject and only one subject that is not shared. Again, the aspects of the present invention described herein are not limited in this respect, as any number of subjects within a context can be either shared or unshared.

As discussed above, one application for the aspects of the present invention is for managing context in a clinical healthcare environment. While one embodiment of the present invention has been described in connection with the CCOW standard, and its defined subjects (e.g., user subject, patient subject, counter subject, clinical provider subject, observation subject and insurer subject), it should be appreciated that the present invention is not limited to use with a context management system that complies with the CCOW standard, or that manages the identical list of subjects, as other context sharing environments are possible for clinical healthcare environments that do not include the identical subjects defined in precisely the same manner as in the CCOW standard.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the present invention comprises at least one computer-readable medium (e.g., a computer memory, a floppy disk, a compact disk, a tape, etc.) encoded with a computer program (i.e., a plurality of instructions), which, when executed on a processor, performs the above-discussed functions of the embodiments of the present invention. The computer-readable medium can be transportable such that the program stored thereon can be loaded onto any computer system resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

It should be appreciated that in accordance with several embodiments of the present invention wherein processes are implemented in a computer readable medium, the computer implemented processes may, during the course of their execution, receive input manually (e.g., from a user), in the manners described above.

In one embodiment of the present invention, the context manager is implemented on at least one computer that includes at least one processor programmed to perform the above-discussed functions. In addition, the context manager can further include at least one storage element to store information relating to the values of various subjects. The storage element can be a memory, a disk drive, or any other component capable of storing computer readable information.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A method of facilitating execution of a plurality of applications, the method comprising acts of:
   (a) providing an interface between a context manager (CM) and the plurality of applications, each of the plurality of applications being configured to share at least a first subject and a second subject in a first context, the CM being configured to permit the plurality of applications to share the first subject but not the second subject, the interface being configured to permit each one of the plurality of applications to set the second subject and to inform the one of the plurality of applications that the second subject has been set, wherein the CM manager context sharing between the plurality of applications, each context being defined at least in part by subject data for at least one subject usable by the plurality of applications, the subject data comprising, for the at least one subject, a data item having a set of values comprising at least a first value corresponding to a first of the plurality of applications and at least a second value corresponding to a second of the plurality of applications, the set of values identifying the at least one subject in the associated context; and
   (b) maintaining values for the second subject separately for the plurality of applications so that the second subject is not shared among the plurality of applications.

2. The method of claim 1, wherein the first subject is a user subject that identifies a user of the plurality of applications and that, when shared, enables single sign on for the plurality of applications, and wherein the second subject is a different subject.

3. The method of claim 2, wherein the first context comprises a plurality of subjects that includes the first and second subjects, and wherein the CM is configured to prevent the plurality of applications from sharing any of the plurality of subjects other than the user subject.

4. The method of claim 1, wherein the second subject is a user subject that identifies a user of the plurality of applications, and wherein the first subject is a different subject.

5. The method of claim 4, wherein the first context comprises a plurality of subjects that includes the first and second subjects, and wherein the CM is configured to permit the plurality of applications to share all of the plurality of subjects other than the user subject.

6. The method of claim 1, wherein the CM is configured to manage sharing of the first subject according to the CCOW standard.

7. The method of claim 1, wherein the act (a) comprises an act of providing an interface between the CM and the plurality of applications that enables each of the plurality of applications to get a value for the second subject.

8. The method of claim 1, wherein the act (b) is performed by the CM.

9. The method of claim 8, wherein the act (b) comprises an act of maintaining, in the CM, values for the second subject separately for the plurality of applications.

10. The method of claim 1, wherein the second subject is a secured subject.

11. The method of claim 10, wherein the secured subject requires privileges to enable an application to set the secured subject, and wherein the act (a) comprises an act of providing each of the plurality of applications with sufficient privileges to set the secured subject.

12. The method of claim 1, wherein the second subject is an unsecured subject.

13. The method of claim 1, wherein the plurality of applications relate to a clinical healthcare environment, and wherein the first context comprises a plurality of subjects that includes a patient subject.

14. The method of claim 13, wherein the plurality of subjects further comprises an encounter subject and an observation subject.

15. At least one computer readable medium encoded with instructions for execution in a computer system comprising a plurality of applications, the instructions, when executed, performing a method of facilitating execution of the plurality of applications, the method comprising acts of:
  (a) providing an interface between a context manager (CM) and the plurality of applications, each of the plurality of applications being configured to share at least a first subject and a second subject in a first context, the CM being configured to permit the plurality of applications to share the first subject but not the second subject, the interface being configured to permit each one of the plurality of applications to set the second subject and to inform the one of the plurality of applications that the second subject has been set, wherein the CM manages context sharing between the plurality of applications, each context being defined at least in part by subject data for at least one subject usable by the plurality of applications, the subject comprising, for the at least one subject, a data item having a set of values comprising at least a first value corresponding to a first of the plurality of applications and at least a second value corresponding to a second of the plurality of applications, the set of values identifying the at least one subject in the associated context; and
  (b) maintaining values for the second subject separately for the plurality of applications so that the second subject is not shared among the plurality of applications.

16. The at least one computer readable medium of claim 15, wherein the first subject is a user subject that identifies a user of the plurality of applications and that, when shared, enables single sign on for the plurality of applications, and wherein the second subject is a different subject.

17. The at least one computer readable medium of claim 16, wherein the first context comprises a plurality of subjects that includes the first and second subjects, and wherein the CM is configured to prevent the plurality of applications from sharing any of the plurality of subjects other than the user subject.

18. The at least one computer readable medium of claim 15, wherein the second subject is a user subject that identifies a user of the plurality of applications, and wherein the first subject is a different subject.

19. The at least one computer readable medium of claim 18, wherein the first context comprises a plurality of subjects that includes the first and second subjects, and wherein the CM is configured to permit the plurality of applications to share all of the plurality of subjects other than the user subject.

20. The at least one computer readable medium of claim 15, wherein the CM is configured to manage sharing of the first subject according to the CCOW standard.

21. The at least one computer readable medium of claim 15, wherein the act (a) comprises an act of providing an interface between the CM and the plurality of applications that permits each of the plurality of applications to get a value for the second subject.

22. The at least one computer readable medium of claim 15, wherein the act (b) is performed by the CM.

23. The at least one computer readable medium of claim 22, wherein the act (b) comprises an act of maintaining, in the CM, values for the second subject separately for the plurality of applications.

24. The at least one computer readable medium of claim 15, wherein the second subject is a secured subject.

25. The at least one computer readable medium of claim 24, wherein the secured subject requires privileges to enable an application to set the secured subject, and wherein the act (a) comprises an act of providing each of the plurality of applications with sufficient privileges to set the secured subject.

26. The at least one computer readable medium of claim 15 wherein the second subject is an unsecured subject.

27. The at least one computer readable medium of claim 15, wherein the plurality of applications relate to a clinical healthcare environment, and wherein the first context comprises a plurality of subjects that includes a patient subject.

28. The at least one computer readable medium of claim 27, wherein the plurality of subjects further comprises an encounter subject and an observation subject.

29. A context manager (CM) for use in a computer system comprising a plurality of applications, the context manager comprising:
  at least one processor programmed to mange context sharing between the plurality of applications, each context being defined at least in part by subject data for at least one subject usable by the plurality of applications, the subject data comprising, for the at least one subject, a data item having a set of values comprising at least a first value corresponding to a first of the plurality of applications and at least a second value corresponding to a second of the plurality of applications, the set of values identifying the at least one subject in the associated context, wherein the at least one processor is programmed to:
    permit the plurality of applications to share a first subject but not a second subject in a first context;
    provide an interface between the CM and the plurality of applications, each of the plurality of applications being configured to share at least the first and second subjects in the first context, the interface being configured to permit each one of the plurality of applications to set the second subject and to inform the one of the plurality of applications that the second subject has been set; and
    maintain value for the second subject separately for the plurality of application so that the second subject is not shared among the plurality of applications.

30. The context manager of claim 29, wherein the first subject is a user subject that identifies a user of the plurality of applications and that, when shared, enables single sign on for the plurality of applications, and wherein the second subject is a different subject.

31. The context manager of claim 30, wherein the first context comprises a plurality of subjects that includes the first and second subjects, and wherein the at least one processor is programmed to prevent the plurality of applications from sharing any of the plurality of subjects other than the user subject.

32. The context manager of claim 29, wherein the second subject is a user subject that identifies a user of the plurality of applications, and wherein the first subject is a different subject.

33. The context manger of claim 32, wherein the first context comprises a plurality of subjects that includes the first and second subjects, and wherein the at least one processor is programmed to permit the plurality of applications to share all of the plurality of subjects other than the user subject.

34. The context manager of claim 29, wherein the at least one processor is programmed to manage sharing of the first subject according to the CCOW standard.

35. The context manager of claim 29, wherein the at least one processor is programmed to provide an interface between the CM and the plurality of applications that permits each of the plurality of applications to get a value for the second subject.

36. The context manager of claim 29, further comprising at least one storage element, and wherein the at least one processor is programmed to separately maintain, in the at least one storage element, values for the second subject for the plurality of applications.

37. The context manager of claim 29, wherein the second subject is a secured subject.

38. The context manager of claim 37, wherein the secured subject requires privileges to enable an application to set the secured subject, and wherein the at least one processor is programmed to provide each of the plurality of applications with sufficient privileges to set the secured subject.

39. The context manager of claim 29, wherein the second subject is an unsecured subject.

40. The context manager of claim 29, wherein the plurality of applications relate to a clinical healthcare environment, and wherein the first context comprises a plurality of subjects that includes a patient subject.

41. The context manager of claim 40, wherein the plurality of subjects further comprises an encounter subject and an observation subject.

* * * * *